United States Patent [19]

Amiet

[11] Patent Number: 4,760,177

[45] Date of Patent: Jul. 26, 1988

[54] PROCESS FOR PREPARING ALKALI METAL SALTS OF TRIFLUOROACETIC ACID IN THE ANHYDROUS AND CRYSTALLINE STATE

[75] Inventor: Louis Amiet, Lyons, France

[73] Assignee: Rhone Poulenc Specialties Chimiques, Courbevoie, France

[21] Appl. No.: 920,596

[22] Filed: Oct. 20, 1986

[30] Foreign Application Priority Data

Oct. 18, 1985 [FR] France ................ 85 15462

[51] Int. Cl.$^4$ ............................................. C07B 53/21
[52] U.S. Cl. ................................................. 562/605
[58] Field of Search ........................................ 562/605

[56] References Cited

U.S. PATENT DOCUMENTS

| 2,920,086 | 1/1960 | Barnhart et al. | 562/605 X |
| 3,997,599 | 12/1976 | Grinstead | 562/605 X |
| 4,049,681 | 9/1977 | Dietrich et al. | 562/605 X |

FOREIGN PATENT DOCUMENTS 891858 3/1962 United Kingdom .

*Primary Examiner*—Donald B. Meyer
*Assistant Examiner*—Patricia M. Scott
*Attorney, Agent, or Firm*—Finnegan, Henderson, Farabow, Garrett and Dunner

[57] ABSTRACT

A process for preparing alkali metal salts of trifluoroacetic acid in the anhydrous and crystalline state. In a first stage, trifluoroacetic acid is neutralized with an alkaline agent in a medium consisting essentially of an alcohol containing 3 to 4 carbon atoms. In a second stage, the water formed by the neutralization reaction is removed by azeotropic distillation. In a third state, the remainder not removed by distillation in the second stage is treated by adding a hydrocarbon which does not solubilize an alkali metal trifluoroacetate and which forms an azeotrope with the alcohol to separate crystals of anhydrous alkali metal trifluoroacetate.

18 Claims, No Drawings

PROCESS FOR PREPARING ALKALI METAL SALTS OF TRIFLUOROACETIC ACID IN THE ANHYDROUS AND CRYSTALLINE STATE

The present invention relates to a process for preparing crystals of alkali metal trifluoroacetates. It relates more especially to a process for preparing crystals of anhydrous alkali metal trifluoroacetates.

An anhydrous salt of trifluoroacetic acid is defined herein as a salt containing less than 0.1% of water.

It is known from the Journal of the American Chemical Society 76, 4285-7 (1954) to prepare sodium trifluoroacetate by neutralization of an aqueous solution of trifluoroacetic acid using sodium carbonate, followed by filtration, evaporation to dryness and drying under vacuum at approximately 100° C. However, it has also been known for a very long time [Bulletin de L'Academie Royale de Belgique Vol. 8, 343-370 (1922)] that "sodium trifluoroacetate crystallizes from its aqueous solution only when the evaporation in a desiccator is taken to almost complete dryness." The author of this article states subsequently that this dryness is virtually impossible to attain.

In effect, from the experiments carried out and in the light of the extreme hygroscopicity of alkali metal salts of trifluoroacetic acid, it is impossible industrially to obtain crystals of alkali metal salts of trifluoroacetic acid from their aqueous solution by simple evaporation. This is because, when an aqueous solution of alkali metal trifluoroacetate is subjected to evaporation, an extremely viscous liquid is obtained, within which crystallization becomes virtually impossible, even on addition of crystals to initiate the crystallization.

A method has been attempted which consists of allowing an aqueous solution of alkali metal salts of trifluoroacetic acid to flow into a heated and stirred organic solvent such as toluene, followed by removing the water by azeotropic distillation. On a small scale, this technique is usable, but on an industrial scale, it is impossible to implement. In effect, the aqueous phase introduced tends rapidly to agglomerate and form a second distinct liquid phase.

Even if the organic phase is brought to a temperature in the region of its boiling point, so as to remove the maximum amount of water, it is not possible to decrease the water content sufficiently and avoid this separation of the aqueous phase.

This aqueous phase tends to solidify when dehydrated, resulting in the formation of lumps which are difficult to extract from the industrial apparatus. In effect, to extract the latter, it would be necessary to melt the collected mass, but the melting point of alkali metal trifluoroacetates (205° C., for example, for the sodium salt) is too close to that at which they decompose (208° C., for example, for the sodium salt) to be able to contemplate a procedure of this nature.

Thus, none of the processes of the prior art enables alkali metal salts of trifluoroacetic acid to be obtained industrially in the anhydrous and crystalline state.

The present invention, which can obtain this objective, is a process for preparing alkali metal salts of trifluoroacetic acid in the crystalline state, preferably in the anhydrous and crystalline state, comprising the steps of: (a) in a first stage, neutralizing trifluoroacetic acid with an alkaline agent in a medium consisting essentially of an alcohol containing 3 to 4 carbon atoms; (b) in a second stage, removing by azeotropic distillation the water formed by the neutralization reaction; and (c) in a third stage, treating the remainder not removed by distillation in the second stage with a hydrocarbon which does not solubilize an alkali metal trifluoracetate and which forms an azeotrope with the alcohol to separate crystals of alkali metal trifluoroacetate, preferably anhydrous alkali metal trifluoroacetate.

Representative hydrocarbons which do not solubilize an alkali metal trifluoroacetate and which form an azeotrope with the alcohol include cyclohexane, benzene and, preferably, toluene.

The alcohol used as a neutralizing medium includes the propanols and the butanols. Preferably, a butanol is used because (1) butanols form azeotropes with water having boiling points sufficiently different from those of the pure alcohols that separation is facilitated; and (2) butanols form with hydrocarbons azeotropes having boiling points sufficiently different from that of the pure hydrocarbon that separation is facilitated. As an additional advantage, these azeotropes, as well as the pure alcohols, have a boiling point sufficiently different from the melting point of alkali metal trifluoroacetates to avoid the decomposition of the alkali metal trifluoroacetates.

Representative alkaline neutralizing agents include the alkali metal hydroxides, carbonates and hydrogen carbonates. It is preferable to use the carbonates, which form less water during the neutralization of the trifluoracetic acid.

After the neutralization step, the water is removed by azeotropic distillation, preferably with the alcohol as mentioned above.

The hydrocarbon toluene is then preferably added to the remainder not removed by the distillation in the second stage. The toluene induces the precipitation of the alkali metal trifluoroacetate, in contrast to the results obtained in the previous experiments utilizing an aqueous medium.

To avoid losses of salts which would remain dissolved in the alcohol/hydrocarbon mixture, it is preferable, in a first step of carrying out the third stage, to distill the alcohol/hydrocarbon azeotrope to remove all the alcohol. During this distillation, and with an optional further addition of hydrocarbon, crystallization occurs and the crystals are recovered by simple filtration under a dry atmosphere and then taken to an oven heated at approximately 100°-120° C.

The constituents of the alcohol/water and alcohol/hydrocarbon azeotropes can be separated in a known manner.

During the first stage, an approximately stoichiometric amount of alkaline neutralizing agent is used relative to the amount of trifluoroacetic acid to be neutralized. For a better implementation of the process according to the invention, when the neutralizing agent is a carbonate, it is preferable to use a slight excess of trifluoroacetic acid with respect to the stoichiometric amount to avoid the situation where crystals of alkali metal trifluoroacetate surround unchanged carbonate, and then, when everything is dissolved, to complete the neutralization using alkali metal hydroxide in concentrated aqueous solution.

A mole ratio of the alkali metal carbonate to trifluoroacetic acid of from about 0.475 to 0.5 is preferably used.

A ratio by weight of trifluoroacetic acid to the alcohol of preferably from about 0.4:1 to 5:1 and more preferably, 1.15:1 to 1.18:1 is used.

An especially advantageous embodiment of the process consists of using as the neutralization medium the azeotrope consisting of approximately 55% by weight of 2-butanol and 45% by weight of toluene.

The water formed by the neutralization reaction is then removed in the form of a water/2-butanol/toluene ternary system, which separates into two layers after condensation. After removal of the water, toluene is added to the reaction medium in sufficient amounts to enable the 2-butanol to be removed in the form of a 2-butanol/toluene azeotrope, and to form the medium for precipitation of the alkali metal trifluoroacetate. The toluene/2-butanol azeotrope can be reused for a fresh first neutralization stage.

Alkali metal trifluoroacetates are used as a perfluoroalkylating agent for the manufacture of organic intermediates in the pharmaceutical and plant-protection industry and thus have a well-known utility. (Patent J 57-139,025).

The invention will be described more completely by means of the examples which follow, which are not to be regarded as limiting the invention.

EXAMPLE 1A

Use of 1-butanol—Preparation of $CF_3COONa$ 250 g of 1-butanol and 53 g of pure $Na_2CO_3$ are introduced into a 1-liter glass round-bottomed flask surmounted by a glass distillation column and equipped with a stirrer, a thermometer and a dropping funnel. With brisk stirring, 115 g, corresponding to 1 mole, of trifluoroacetic acid of purity greater than 99% are introduced in the course of 1 hour. The temperature in the flask rises naturally to approximately 40° C. Stirring is maintained for 15 minutes after the addition is complete, and the complete disappearance of the carbonate crystals is observed. The flask is heated and a mixture is distilled under atmospheric pressure at a temperature of 92° C. at the head of the column, this mixture settling into two phases after condensation.

The distillation is continued: the temperature at the head reaches 116.5°–117° C.; heating is stopped when the remaining volume is approximately 100 cm³. The mixture is cooled to room temperature and no crystallization is observed. Approximately 200 cm³ of toluene are then added slowly and with gentle stirring, and the formation of a white crystalline precipitate is observed. The precipitate is filtered off, rinsed with approximately 25 cm³ of toluene and dried in an oven at 120° C. 105 g (0.77 mole) of dry crystals of $CF_3COONa$ are thereby obtained (yield=77%).

EXAMPLE 1B

The same apparatus as for Example 1A is used

The flask is charged with 200 g of 1-butanol and 106 g of pure $Na_2CO_3$. With stirring, 235 g of trifluoroacetic acid (purity greater than 99%) are allowed to run in, taking approximately 30 minutes.

The temperature in the flask rises from 25° C. to 55° C.

The flask is then heated and a homogeneous solution is observed at 90° C. A sample is withdrawn, in which it is found that the pH is 1, and it is brought back to 6 by a dropwise addition of an approximately 50% strength aqueous solution of NaOH; 3 g of this solution are required for this purpose. The reaction mixture is heated to reflux and a mixture is distilled at 89°–90° C. at the head of the column, which mixture separates into two layers after condensation (the distillation is stopped as soon as the temperature begins to rise above 90° C.): a dense layer weighing 13 g and a light layer weighing 22 g. At the end of this distillation, the initiation of a precipitation is observed. The temperature in the flask, 119° C. at the beginning of the distillation and 129° at the end, is then brought back to 105°–110° C., and 300 g of toluene are then added, with the stirring being maintained. A mixture weiqhing 484 g is then distilled which comes over at the beginning at a temperature of 100° C. at the head, rising slowly to 105° C., while toluene is fed in continuously, followed by a second fraction which comes over at 105° C. and weighs 348 g; the mass of toluene added during the distillation is 600 g. The temperature at the head then rises fairly quickly to 109° C. while a further 45 g of toluene are distilled. The distillation is then stopped, the flask cooled to approximately 30° C. and its contents passed through a filter. The weight of precipitate impregnated with toluene is 295 grams, and after being dried in an oven at 115° C., weighs 270 grams (yield approximately 97%).

EXAMPLE 2

Use of isobutanol (or 2-methyl-1-propanol)

The same assembly is used as in Example 1.

106 g of pure $Na_2CO_3$ and 200 g of isobutanol are introduced into the flask, followed by 230.3 g (2 moles) of trifluoroacetic acid (TFA) added in the course of 30 minutes with stirring. The mixture is heated to reflux and it is observed that dissolution is complete after one hour. A mixture is then distilled at 87.5°–89° C. at the head of the column, which mixture settles into two layers, and then, from 89° to 108° C., an intermediate fraction weighing 22 g is distilled. 412 g of toluene are gradually added from a dropping funnel at a rate such that the level in the flask remains substantially constant as the distillation is continued. A white precipitate is gradually formed. In this manner, there are distilled, at 98°–99.5° C. at the head of the column, a fraction weighing 314 g, then from 99.5° to 110° C., a fraction weighing 21 g, and finally 50 g at this latter temperature of 110° C. The flask is cooled to room temperature and its contents are then filtered on a sintered glass filter. The precipitate collected, impregnated with toluene, weighs 293 g, and after being dried for 3 hours in an oven at 115° C., weighs 267 g, which corresponds to a 97.4% yield of anhydrous sodium trifluoroacetate, which takes the form of fine white crystals. Thermal analysis shows that the sodium trifluoroacetate melts at about 208° C., followed by decomposition at about 212° C. The water content, determined by the K. Fisher method on the dried product, indicates a value of 400 mg/kg.

EXAMPLE 3

A fresh preparation of $CF_3COONa$ is performed as above, but in a 6-liter round-bottomed flask.

848 g (8 moles) of pure $Na_2CO_3$ and 1,600 g of isobutanol are used. 1,892.4 g (16.45 moles) of $CF_3COOH$ are introduced into the stirred suspension in the course of 1 hour 30 min. $CO_2$ is allowed to evolve freely.

The temperature is brought to 85° C. and, after 15 min., it is observed that the whole reaction medium has become clear. An approximately 50% strength aqueous solution of pure NaOH is gradually added until a pH of 5 to 6 is obtained, which requires 42 g of alkaline solution.

Distillation of the isobutanol/$H_2O$ azeotrope is then performed, the temperature at the head of the column being between 86° and 89° C., and that in the flask rising from 108° to 118° C. The distillate settles into two layers:

1 dense aqueous phase weighing 102 g, containing approximately 90% of water; and 1 upper phase weighing 415 g, containing approximately 10% of water.

The distillation is continued and a further fraction, coming over at between 98° and 100° C., weighing 220 g and containing 4.9% of water, is separated.

The flask is cooled to 95° C., and 950 g of toluene are added while this temperature is maintained. It is observed that the medium is still homogeneous. 920 g of toluene are then added gradually, with slow stirring, and the start of crystallization is observed as soon as the addition of toluene is resumed. The distillation is then resumed while stirring is maintained and toluene is simutaneously fed in. In this manner, the following are separated:

a small fraction weighing 41 g, coming over at from 76° to 90° C., from which 2 g of aqueous phase settle; and then a fraction weighing 2,262 g, coming over at 99°-100° C., containing 0.4% of water, 43.2% of isobutanol and 56.4% of toluene.

The additional charge of toluene is 1,000 g, added during the distillation of these two fractions. The feeding of toluene is then stopped and the distillation continued.

The head temperature rises to 109° C. and a final fraction weighing 385 g, consisting of toluene and containing 220 ppm of water, is separated.

The flask is cooled, and the precipitate is filtered and dried in an oven as before at 115° C. The mass of $CF_3COONa$ collected, containing 480 ppm of water according to analysis, is 2,198 g (16.16 moles). An approximately 98% yield of sodium trifluoroacetate is obtained.

EXAMPLE 4

Preparation of solid $CF_3COO$ Li—Use of isobutanol

The apparatus of Example No. 1 is used. 74 g of pure $Li_2CO_3$ and 200 g of isobutanol are introduced into the flask, and 234.8 g of $CF_3COOH$ (2.04 moles) are then added from the funnel, in the course of 1 hour, to the contents of the flask. The flask is then heated to 80° C. The pH of the medium is approximately 1. A saturated aqueous solution of pure lithium hydroxide is then added until the pH reaches 5. A liquid is then distilled at 88°-89° C. at the head, which mixture settles into two phases, the lower water-rich phase weighing 21 g and the upper phase 74 g. A fraction weighing 25 g corresponding to 89° to 106° C. at the head of the column is then separated, the temperature in the flask reaching 138° C. The mixture is allowed to cool to 95° C., 400 g of toluene are then introduced and the distillation is resumed. In this manner, a fraction weighing 328 g is separated at 99°-100° C. while 300 g of toluene are introduced into the flask, and a further 50 g are then distilled until 108° C. is reached at the head. The flask is allowed to cool to 50° C. and the solid obtained is filtered off and dried at 115° C. 246 g of product, containing 0.08% of water according to analysis, are obtained. The yield of crystallized anhydrous lithium trifluoroacetate obtained is approximately 99.5%.

EXAMPLE 5

Preparation of $CF_3COOK$

In the same apparatus as above, there are introduced 138 g of pure $K_2CO_3$, 200 g of isobutanol and, according to the same process as above, 235 g (2.04 moles) of $CF_3COOH$. The pH of approximately 1 at the end of the reaction is brought back to 6 by adding approximately 6 g of approximately 50% strength KOH. The same process for separation of the isobutanol/$H_2O$ azeotrope is followed. In this manner, there are successively separated a fraction weighing 61 g at 88°-89° C., which settles into two phases, and then an intermediate fraction weighing 44 g at up to 106° C.

After the flask has been brought back to 95° C., 400 g of toluene are added, and 330 g of toluene/isobutanol azeotropic mixture are distilled at 99°-100° C. while a further 150 g of toluene are added continuously, and a further fraction weighing 50 g is separated at up to 110° C. at the head. After the mixture has been cooled to approximately 50° C. and filtered, and the residue dried, 301 g of product containing 550 ppm of water (0.055%) are recovered. The yield of potassium trifluoroacetate is approximately 96%.

EXAMPLE 6

Use of 2-butanol—Preparation of $CF_3COONa$

In the same apparatus, there are used 106 g of pure $Na_2CO_3$, 200 g of 2-butanol and then, according to the process already described, 235 g (2.04 moles) of $CF_3COOH$ added over the course of one hour. The final pH of approximately 1 is brought back to 5 by adding 4 g of concentrated aqueous NaOH solution.

While gentle agitation is maintained in the flask, the following are distilled:

at 84°-85° C., a fraction weighing 64 g which is homogeneous after condensation, then, at up to 93° C., a fraction weighing 16 g.

The start of crystallization is then observed in the liquid in the flask. After the flask has been cooled, 300 g of toluene are introduced and the distillation is resumed. The following are separated successively:

a fraction weighing 13 g, at up to 93° C. at the head of the column, a fraction weighing 221 g, at 93°-94° C., which analysis shows to contain 54.3% of 2-butanol, a fraction weighing 9 g, at up to 108° C., and finally, a fraction weighing 40 g, at 110° C.

The reaction mixture is cooled to 40° C. and filtered on sintered glass, and the residue dried at 115° C., and 275 g of final product are obtained, which corresponds to a 99% yield of sodium trifluoroacetate.

EXAMPLE 7

In the same apparatus, a mixture of 200 g of 2-butanol with 160 g of toluene, corresponding essentially to the toluene/2-butanol azeotrope, and 106 g of pure $Na_2CO_3$ are introduced in this instance. Proceeding as above, 235 g of $CF_3COOH$ of more than 99% purity, equivalent to 2.04 moles of $CF_3COOH$, are then added per hour, which brings the temperature to 50° C. The mixture is then heated to 70° C. and it is observed that everything has dissolved. The pH is brought back to 5-6 with 50% strength NaOH, and distillation is then carried out.

The following are separated successively:

at 77°-78%°C. at the head of the column, a fraction which separates into two phases, a lower phase weighing 19 g, assaying at 91% of water, and an organic phase weighing 51 g containing, according to analysis, 37% of 2-butanol, 56.2% of toluene and 3.8% of water;

at 93°–94° C. at the head, by continuously adding toluene to the flask to compensate for the volume distilled (which rapidly induces the crystallization of $CF_3COONa$), a distillate weighing 294 g containing, according to analysis, 58.5% of 2-butanol, 40.9% of toluene and 0.28% of water;

from 95° to 109° C., a fraction weighing 10 g, and finally, 50 g at 109°–110° C.

The contents of the flask are, as in the previous examples, filtered and the solid is dried at 115° C. 274 g of product containing 0.08% of water are finally collected, which corresponds to a 97.9% yield of sodium trifluoroacetate.

EXAMPLE 8

Use of isopropanol

In the same apparatus, 200 g of isopropanol and 106 g of $Na_2CO_3$ are introduced, and 235 g (2.04 moles) of $CF_3COOH$ are reacted. When the evolution of $CO_2$ has ceased, the solution is at 50° C. and no solid remains. The pH is brought back to 6 with NaOH and the following are then distilled after a further 50 g of isopropanol have been added:

at 76° C. at the head, a fraction weighing 170 g; after the mixture has cooled to 90° C. and 350 g of toluene are added (which induces the start of precipitation), and the resumption of heating, a fraction weighing 168 g which comes over at 76°–77° C., rising rapidly to 100° C.; and finally, from 100° to 109° C., 50 g.

The mixture is cooled, filtered and dried, and 275 g of sodium trifluoroacetate are obtained, which corresponds to a 99.3% yield.

EXAMPLE 9

Use of 2-butanol, and of cyclohexane in place of toluene. Preparation of sodium trifluoroacetate.

In the same apparatus as above, there are introduced 106 g of pure $Na_2CO_3$, 200 g of 2-butanol and then, according to the process already described, 235 g of trifluoroacetic acid (containing more than 99% of $CF_3COOH$) in the course of approximately 1 hour. As above, the pH is brought back to approximately 5 with a few grams of concentrated NaOH.

The following are separated by distillation:

at 85°–86° C. at the head of the column, a fraction weighing 84 grams, which separates into a dense layer weighing 11 g and a light layer weighing 73 g, and between 86° and 100° C., a fraction weighing 4 g.

The distillation is then stopped and the contents of the flask are cooled to 75° C. 300 g of cyclohexane are added with stirring from the dropping funnel. The separation of the liquid into 2 layers and the start of precipitation of fine white solid ($CF_3COONa$) are then observed.

The distillation is resumed and a fraction weighing 735 grams is separated, at 75°–76° C. at the head of the column, while cyclohexane is added from the dropping funnel so as to maintain an approximately constant liquid level in the distillation flask. The amount of cyclohexane simultaneously introduced is 650 grams.

The distillation is then stopped and the contents of the flask are cooled to approximately 30° C. and then passed through a sintered glass filter. A mass of crystals impregnated with cyclohexane are collected, weighing 290 g, and after drying in an oven at 120° C., the crystals weigh 268 grams, corresponding to an approximately 96–97% yield.

I claim:

1. A process for preparing an alkali metal salt of trifluoroacetic acid in the anhydrous and crystalline state comprising the steps of:
   a. in a first stage neutralizing trifluoroacetic acid with an alkaline agent in a medium consisting essentially of an alcohol containing 3 to 4 carbon atoms;
   b. in a second stage, removing by azeotropic distillation the water formed in the neutralization reaction; and
   c. in a third stage, treating the remainder not removed by azeotropic distillation in the second stage with a hydrocarbon which does not solubilize an alkali metal trifluoroacetate and which forms an azeotrope with the alcohol to separate anhydrous crystals of alkali metal trifluoroacetate.

2. The process of claim 1, wherein the hydrocarbon is selected from the group consisting of cyclohexane, benzene and toluene.

3. The process of claim 2, wherein the hydrocarbon is toluene.

4. The process of claim 1, wherein the alcohol is a butanol.

5. The process of claim 1, wherein the alkaline agent is at least one compound selected from the group consisting of alkali metal hydroxides and alkali metal carbonates.

6. The process of claim 5, wherein the alkaline agent is an alkali metal carbonate and an alkali metal hydroxide.

7. The process of claim 6, wherein the mole ratio of trifluoroacetic acid to the alkaline agent is stoichiometric.

8. The process of claim 7, wherein the mole ratio of the carbonate to trifluoroacetic acid is from about 0.475:1 to 0.5:1, and the amount of alkali metal hydroxide used is sufficient so that the mole ratio of trifluoroacetic acid to the alkaline agent in step a. is stoichiometric.

9. The process of claim 6, wherein the mole ratio of the carbonate to trifluoroacetic acid is from about 0.475:1 to 0.5:1, and the amount of alkali metal hydroxide used is sufficient so that the mole ratio of trifluoroacetic acid to the alkaline agent in step a. is stoichiometric.

10. The process of claim 1, wherein in the third stage, the alcohol is removed by means of an alcohol/hydrocarbon azeotrope.

11. A process for preparing an alkali metal salt of trifluoroacetic acid in the anhydrous and crystalline state comprising the steps of:
    a. in a first stage, neutralizing trifluoroacetic acid with an alkaline agent in a medium consisting of a mixture of toluene and an alcohol containing 3 to 4 carbon atoms;
    b. in a second stage, removing by azeotropic distillation the water formed by the neutralization reaction; and
    c. in a third stage, treating the remainder not removed by distillation in the second stage with additional toluene to separate crystals of anhydrous alkali metal trifluoroacetate.

12. The process of claim 1, wherein the weight ratio of trifluoroacetic acid to the alcohol is from about 0.4:1 to 5:1.

13. The process of claim 12, whenever the said weight ratio is from about 1.15:1 to 1.18:1.

14. The process of claim 13, wherein the yield of crystals of anhydrous alkali metal trifluoroacetate, based on the amount of trifluoroacetic acid, is at least about 96%.

15. The process of claim 1 wherein the medium is selected from the group consisting of 1-butanol, isobutanol, 2-butanol and isopropanol.

16. The process of claim 11 wherein said medium consists of a toluene/2-butanol azeotrope.

17. The process of claim 1 wherein said alkaline agent is sodium carbonate.

18. The process of claim 10, wherein the alcohol/hydrocarbon azeotrope is distilled to remove the alcohol.

* * * * *